United States Patent
Larson et al.

(10) Patent No.: US 9,365,468 B2
(45) Date of Patent: Jun. 14, 2016

(54) METHODS AND SYSTEMS FOR REFORMING AND TRANSALKYLATING HYDROCARBONS

(71) Applicant: UOP LLC, Des Plaines, IL (US)

(72) Inventors: Robert B. Larson, Naperville, IL (US); Jalesh Kalra, Naperville, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 192 days.

(21) Appl. No.: 14/271,025

(22) Filed: May 6, 2014

(65) Prior Publication Data

US 2015/0321976 A1  Nov. 12, 2015

(51) Int. Cl.

| | |
|---|---|
| C07C 5/27 | (2006.01) |
| C07C 4/18 | (2006.01) |
| C07C 6/12 | (2006.01) |
| C10G 35/06 | (2006.01) |
| C10G 35/085 | (2006.01) |
| C10G 35/09 | (2006.01) |
| C07C 6/06 | (2006.01) |
| C07C 5/327 | (2006.01) |
| C07C 7/04 | (2006.01) |
| C07C 7/12 | (2006.01) |

(52) U.S. Cl.
CPC .................. C07C 6/06 (2013.01); C07C 5/2732 (2013.01); C07C 5/327 (2013.01); C07C 7/04 (2013.01); C07C 7/12 (2013.01)

(58) Field of Classification Search
CPC .............. C07C 5/27; C07C 4/18; C07C 6/12; C10G 35/06; C10G 35/085; C10G 35/09
USPC ......... 585/478, 480, 482, 486, 489, 470, 474, 585/319; 208/135, 136, 137, 138, 208 R, 208/254 R
See application file for complete search history.

(56) References Cited

U.S. PATENT DOCUMENTS

| | | |
|---|---|---|
| 4,939,110 A | 7/1990 | Sachtler et al. |
| 6,924,405 B2 | 8/2005 | Mohr |

(Continued)

FOREIGN PATENT DOCUMENTS

| | | |
|---|---|---|
| CN | 101993334 B | 12/2013 |
| WO | 2009117000 A1 | 9/2009 |
| WO | 2012026956 A1 | 3/2012 |

OTHER PUBLICATIONS

Search Report dated Jul. 30, 2015 for corresponding PCT Appl. No. PCT/US2015/027211.
Alario, et al., "Boost You Xylene Loop Performance With OPARIS," IFP Kinetic and Catalysis Division, Axens Technology Division, Web Article.

(Continued)

Primary Examiner — Thuan D Dang

(57) ABSTRACT

Methods and systems for reforming and transalkylating hydrocarbons are disclosed. A method for processing a hydrocarbon stream includes the steps of separating para-xylene from a first mixed-xylene and ethylbenzene-containing stream to produce a first non-equilibrium xylene and ethylbenzene stream and isomerizing the first non-equilibrium xylene and ethylbenzene stream to produce additional para-xylene. The method further includes transalkylating a toluene stream to produce a second mixed-xylene and ethylbenzene-containing stream, separating para-xylene from the second mixed-xylene and ethylbenzene-containing stream to produce a second non-equilibrium xylene and ethylbenzene stream, and isomerizing the second non-equilibrium xylene and ethylbenzene stream using an ethylbenzene dealkylation type xylene isomerization process to produce additional para-xylene.

7 Claims, 2 Drawing Sheets

(56) References Cited

U.S. PATENT DOCUMENTS

| | | |
|---|---|---|
| 7,314,601 B2 | 1/2008 | Negiz et al. |
| 7,456,125 B2 | 11/2008 | Bogdan et al. |
| 8,084,657 B2 | 12/2011 | Kong et al. |
| 2008/0146859 A1 | 6/2008 | Rekoske et al. |
| 2009/0032386 A1 | 2/2009 | Negiz et al. |
| 2010/0179360 A1 | 7/2010 | Ichioka et al. |
| 2013/0123558 A1 | 5/2013 | Bogdan et al. |

OTHER PUBLICATIONS

Guillon, et al., "How to Improve the Selectivity of Zeolitic Catalysts in C8 Aromatic Cut Isomerization," Oil & Gas Science and Technology—Rev. IFP, vol. 64 (2009), No. 6, pp. 731-744.

Tsai, "Study on Ethylbenzene and Xylene Conversion Over Modified ZSM-5," Applied Catalysis A: General 321, (2007), 125-134.

Zhang, et al., "Study on the Selection of C8 Aromatics Isomerization Technology," Petroleum Processing and Petrochemicals, v 39, n 6, p. 56-59, Jun. 2008.

METHODS AND SYSTEMS FOR REFORMING AND TRANSALKYLATING HYDROCARBONS

TECHNICAL FIELD

The technical field relates generally to hydrocarbon processing methods and systems. More particularly, the technical field relates to methods and systems for reforming and transalkylating hydrocarbons, such as naphtha hydrocarbons.

BACKGROUND

The reforming of petroleum raw materials is an important process for producing useful products. One important process is the separation and upgrading of hydrocarbons for a motor fuel, such as producing a naphtha feedstream and upgrading the octane value of the naphtha in the production of gasoline. However, hydrocarbon feedstreams from a raw petroleum source include the production of useful chemical precursors for use in the production of plastics, detergents and other products.

Xylene isomers ("xylenes") and benzene are produced in large volumes from petroleum by the reforming of naphtha. However, neither the xylenes nor benzene are produced in sufficient volume to meet demand. Consequently, other hydrocarbons are necessarily converted to increase the yield of the xylenes and benzene via processes such as transalkylation, disproportionation, isomerization, and dealkylation. For example, toluene commonly is disproportionated to yield benzene and $C_8$ aromatics from which the individual xylene isomers are recovered.

In addition to xylene, some ethylbenzene is produced using the above-noted processes. However, there is a large difference in ethylbenzene (EB) concentration between mixed xylenes produced by transalkylation versus reforming. Modern transalkylation catalysts have a high dealkylation activity, which results in low yield of EB (about 1% of the $C_8$ aromatic fraction). Reforming catalysts, in contrast, have low cracking activity and generate high concentrations of EB (about 14% of $C_8$ aromatics).

In para-xylene purification processes, it is a requirement to convert EB to prevent accumulation in the recycle loops. Xylene isomerization processes may convert EB through either dealkylation or isomerization reactions. The dealkylation reaction converts EB to form benzene, while the isomerization reaction converts EB to xylene. EB isomerization is equilibrium limited reaction and requires increased hydraulic flow, increased energy consumption, and a high concentration of precious metals. The main advantage of EB isomerization is that it provides the highest yield of desirable para-xylene. EB dealkylation is not limited by equilibrium and therefore requires lower capital, lower energy, and much less precious metal. The drawback of EB dealkylation is that the para-xylene yield is much lower than EB isomerization.

In a typical aromatics complex, the mixed xylene produced by both isomerization processes and reforming processes are combined in a xylene splitter. The mixing of these two streams reduces the concentration of EB to a near equilibrium level. Because the feed is at equilibrium there is limited driving force to form xylene from EB using an EB isomerization process. Thus, the production of xylenes remains suboptimal.

Accordingly, it is desirable to provide improved methods and systems for reforming and transalkylating hydrocarbons. It is further desirable to provide such methods and systems that are able to efficiently convert the produced ethylbenzene to xylenes. Furthermore, other desirable features and characteristics of the presently disclosed embodiments will become apparent from the subsequent detailed description and the appended claims, taken in conjunction with the accompanying drawings and this background.

BRIEF SUMMARY

Methods and systems for reforming and transalkylating hydrocarbons are disclosed. In one exemplary embodiment, a method for processing a hydrocarbon stream includes the steps of separating para-xylene from a first mixed-xylene and ethylbenzene-containing stream to produce a first non-equilibrium xylene and ethylbenzene stream and isomerizing the first non-equilibrium xylene and ethylbenzene stream to produce additional para-xylene. The method further includes transalkylating a toluene stream to produce a second mixed-xylene and ethylbenzene-containing stream, separating para-xylene from the second mixed-xylene and ethylbenzene-containing stream to produce a second non-equilibrium xylene and ethylbenzene stream, and isomerizing the second non-equilibrium xylene and ethylbenzene stream using an ethylbenzene dealkylation type xylene isomerization process to produce additional para-xylene.

In another exemplary embodiment, a system for processing a hydrocarbon stream includes a first para-xylene separating unit that separates para-xylene from a first mixed-xylene and ethylbenzene-containing stream to produce a first non-equilibrium xylene and ethylbenzene stream and an isomerization unit that isomerizes the first non-equilibrium xylene and ethylbenzene stream to produce additional para-xylene. The system further includes a transalkylation unit that transalkylates a toluene stream and a $C_{9+}$ aromatic streams to produce a second mixed-xylene and ethylbenzene-containing stream, a second para-xylene separating unit that separates para-xylene from the second mixed-xylene and ethylbenzene-containing stream to produce a second non-equilibrium xylene and ethylbenzene stream, and an ethylbenzene dealkylation type xylene isomerization unit that dealkylates the second non-equilibrium xylene and ethylbenzene stream to produce additional para-xylene.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Various embodiments contemplated herein relate to methods and systems for reforming and transalkylating hydrocarbons. Various values of temperature, pressure, flow rates, number of stages, feed entry stage number etc. are recited in association with the specific examples described below; those conditions are approximate and merely illustrative, and are not meant to limit the described embodiments. Additionally, for purposes of this disclosure, when the terms "middle", "top" or "lower" are used with respect to a column, these terms are to be understood as relative to each other, i.e. that withdrawal of a stream from the "top" of the column is at a higher position than the stream withdrawn from a "lower" portion of the column. When the term "middle" is used it implies that the "middle" section is somewhere between the "upper" and the "lower" section of the column. However, when the terms "upper", "middle" and "lower" have been used with respect to a distillation column it should not be understood that such a column is strictly divided into thirds by these terms.

Figure 1A:
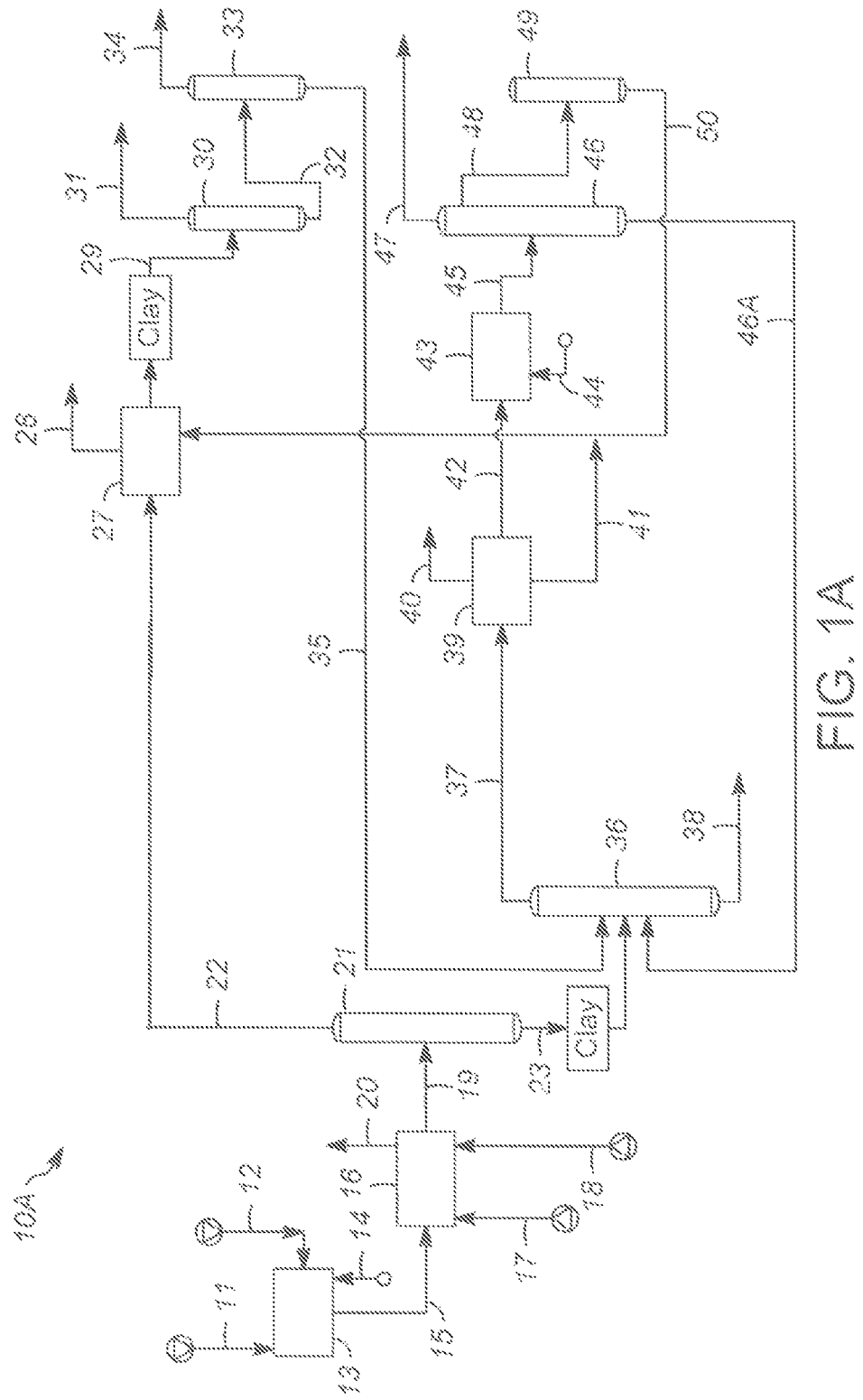
FIGS. 1A and 1B are schematic illustrations of a system and a method for reforming and transalkylating hydrocarbons, such as naphtha hydrocarbons, in accordance with exemplary embodiments.
Figure 1B:
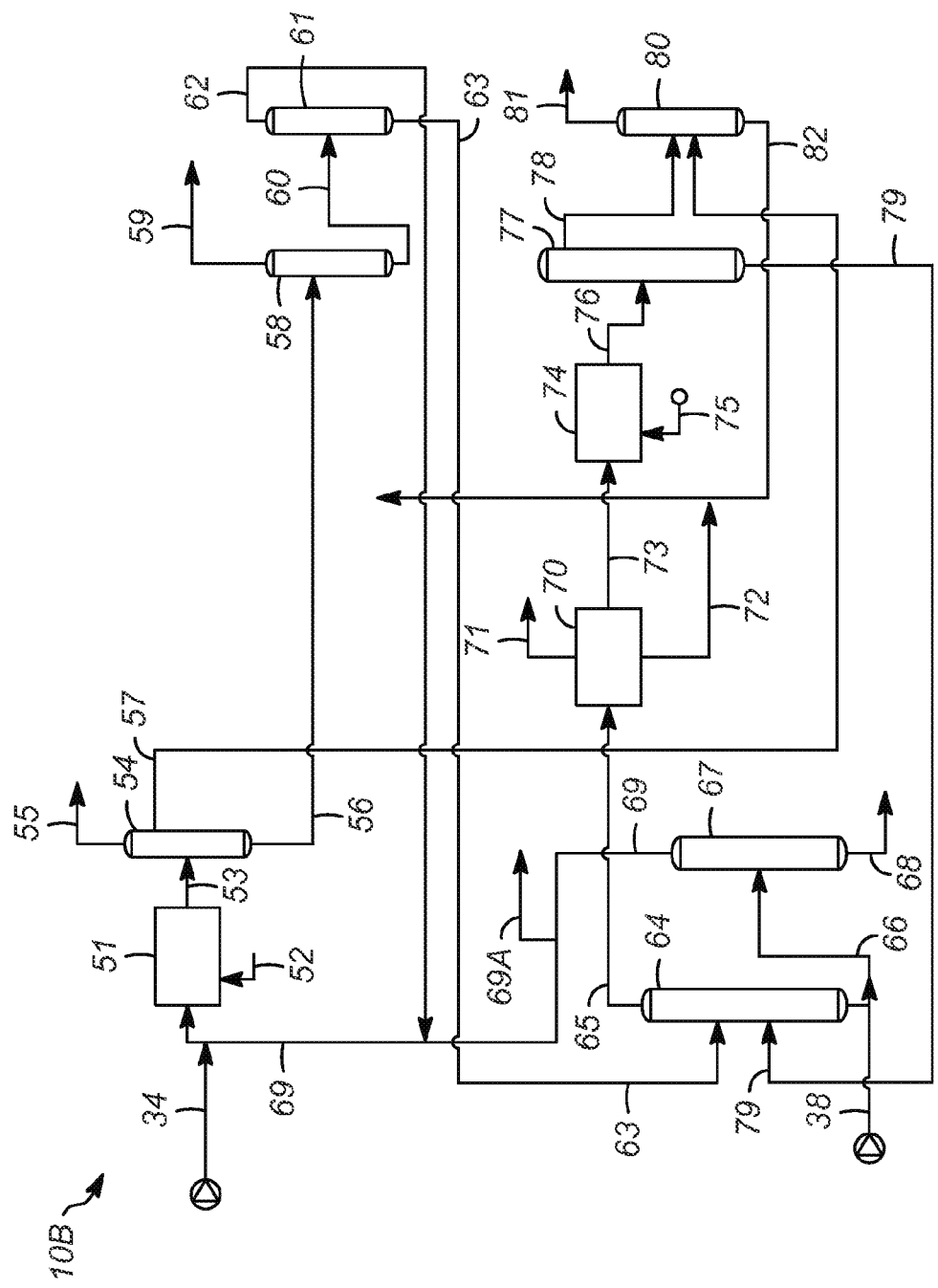

FIGS. 1A and 1B are schematic illustrations of a system 10 (including portions 10A and 10B, respectively) employing a method for reforming and transalkylating hydrocarbons, with FIG. 1A showing the reforming portions thereof and FIG. 1B showing the transalkylating portions thereof. With reference first to FIG. 1A, it is generally appreciated that the reforming of a hydrocarbon feedstream to increase the aromatics content is important for enhancing the value of the hydrocarbon stream. Aromatics, such as benzene and toluene are high value chemicals and are used in a variety of processes to generate downstream products. Examples include alkylaromatic compounds for detergents, ethyl benzene and cumene. The reforming process can include endothermic reactions and can affect the efficiency due to process control of the temperatures of the reactors.

Naptha hydrocarbons may be provided from any suitable source. In FIG. 1A, a plurality of naphtha sources 11 and 12 may be provided, where naphtha source 11 may include a light hydrocarbon naphtha and naphtha source 12 may include a market source of naphtha hydrocarbons. The naphtha sources 11 and 12 may be fed to a hydrotreating zone 13. For the purposes of this disclosure, "hydrotreating" refers to a processing zone 13 where a hydrogen-containing treat gas 14 is used in the presence of suitable catalysts that are primarily active for the removal of heteroatoms, such as sulfur and nitrogen. The hydrotreating zone 13 may contain a single or multiple reactors (preferably trickle-bed reactors) and each reactor may contain one or more reaction zones with the same or different catalysts.

The hydrotreating zone 13 operates to reduce the levels of sulfur and other contaminates to produce a hydrotreated product 15 at the appropriate quality levels to be used as feedstock to a catalytic hydrocarbon reformer (described below). The naphtha hydrocarbons and hydrogen treat gas 14 are contacted with a suitable catalyst at hydrotreating conditions to reduce the level of contaminates in the hydrocarbonaceous stream to generally meet desired levels of sulfur, nitrogen and hydrogenation. For example, the hydrotreating reaction zone 13 may produce a hydrotreated product 15 having a reduced concentration of sulfur of 20 to less than 1 ppm by weight, or, in some embodiments, less than 1 ppm by weight. A reduced concentration of nitrogen of less than 30 ppm by weight, more preferably 0.2 to 1 ppm by weight. The exact contaminate reduction depends on a variety of factors such as the quality of the feedstock, the hydrotreating conditions, the available hydrogen, and the hydrotreating catalyst, among others.

The hydrotreating zone 13 in one aspect operates at relatively mild conditions generally not over 454° C. (850° F.) and 17.3 MPa (2500 psig) in order to reduce over treating the higher boiling hydrocarbons. At severe conditions, a high degree of cracking occurs, often cracking the desired products, such as naphtha, to less valuable light ends. In general, the hydrotreating reaction zone 13 operates at a temperature from 315° C. (600° F.) to 426° C. (800° F.), a pressure from 3.5 MPa (500 psig) to 17.3 MPa (2500 psig), and a liquid hourly space velocity from 0.1 $hr^{-1}$ to 10 $hr^{-1}$. Suitable hydrotreating catalysts for use herein are any known conventional hydrotreating catalyst and include those that are comprised of at least one Group VIII metal (preferably iron, cobalt and nickel, and more preferably cobalt and/or nickel) and at least one Group VI metal (preferably molybdenum and/or tungsten) on a high surface area support material, preferably alumina Other suitable hydrotreating catalysts include zeolitic catalysts, as well as noble metal catalysts where the noble metal is selected from palladium and platinum. It is within the scope herein that more than one type of hydrotreating catalyst can be used in the same reaction vessel. The Group VIII metal is typically present in an amount ranging from 2 to 20 weight percent, preferably from 4 to 12 weight percent. The Group VI metal will typically be present in an amount ranging from 1 to 25 weight percent, preferably from 2 to 25 weight percent. Of course, the particular catalyst compositions and operating conditions may vary depending on the particular hydrocarbons being treated, the concentration of heteroatoms and other parameters.

The hydrotreated naphtha is then passed to a reforming zone 16. Addition naphtha sources may be added to the reforming zone 16, such as naphtha source 17, which may be a diesel hydrocracker heavy naphtha, and naphtha source 18, which may be a gas oil hydrocracker heavy naphtha. The reforming process is a common process in the refining of petroleum, and is usually used for increasing the amount of gasoline. The reforming process comprises mixing a stream of hydrogen and a hydrocarbon mixture and contacting the resulting stream with a reforming catalyst. The reforming reactors are operated with a feed inlet temperature between 450° C. and 540° C. The reforming reaction converts paraffins and naphthenes through dehydrogenation and cyclization to aromatics. The dehydrogenation of paraffins can yield olefins, and the dehydrocyclization of paraffins and olefins can yield aromatics.

The reforming process is an endothermic process, and to maintain the reaction, the reformer is a catalytic reactor that can comprise a plurality of reactor beds with interbed heaters. The reactor beds are sized with the interbed heaters to maintain the temperature of the reaction in the reactors. A relatively large reactor bed will experience a significant temperature drop, and can have adverse consequences on the reactions. The catalyst can also pass through inter-reformer heaters to bring the catalyst up to the desired reformer inlet temperatures. The interbed heaters reheat the catalyst and the process stream as the catalyst and process stream flow from one reactor bed to a sequential reactor bed within the reformer. The most common type of interbed heater is a fired heater that heats the fluid and catalyst flowing in tubes. Other heat exchangers can be used.

Reforming catalysts generally comprise a metal on a support. The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here. The metals preferably are one or more Group VIII noble metals, and include platinum, iridium, rhodium, and palladium. Typically, the catalyst contains an amount of the metal from about 0.01% to about 2% by weight, based on the total weight of the catalyst. The catalyst can also include a promoter element from Group IIIA or Group WA. These metals include gallium, germanium, indium, tin, thallium, and lead.

The reforming zone produces a reformate product stream 19 and an $H_2$-rich net gas stream 20. The reformate product stream 19 can be passed to a reformate splitter 21 to generate a reformate splitter overhead stream 22 including $C_6$ and $C_7$ aromatics, and a bottoms stream 23 including $C_8$ and heavier aromatics. The reformate overhead stream 22 is passed to an aromatics recovery unit 27 thereby generating an aromatics product stream 29 including benzene and toluene. The aromatics recovery unit additionally generates a raffinate stream 28 including paraffins. One industry standard for an aromatics recovery unit 27 is the Sulfolane™ process, which is an extractive distillation process utilizing sulfolane to facilitate high purity extraction of aromatics. The Sulfolane™ process is well known to those skilled in the art. Aromatics product stream 29 may be further separated using a series of fractionation columns 30 and 33, wherein fractionation column 30 receives product stream 29 and produces an overhead benzene product 31, and fractionation column 33 receives the bottoms product 32 from fractionation column 30 and produces an overhead toluene product 34. The bottoms product 35 from fractionation column 33 may include xylenes, and as such may be recycled for xylene fractionation, as will be described in greater detail below.

Returning to the discussion of the reformate splitter 21, the splitter bottoms stream 23 proceeds to a xylene fractionation column 36 that produces a xylene-containing hydrocarbon stream 37 as its overhead product, and heavier hydrocarbons as its bottoms product 38. As noted above, fractionation column 33 bottoms product stream 35 may join stream 23 in the xylene fractionation column 36. As initially noted above, as a result of the reforming process, ethylbenzene is produced, in an amount that may be about 14% of the $C_8$ hydrocarbons produced.

Xylene-containing hydrocarbon stream 37 may thereafter be passed to a para-xylene separation zone 39. Para-xylene is almost exclusively separated from xylene mixtures using simulated moving bed (SMB) technology. The SMB process is a commercial adsorptive separation process using several adsorption beds and moving the inlet streams and outlet streams between the beds, where a process stream comprising para-xylene is passed through the beds. The adsorption beds comprise an adsorbent for preferentially adsorbing the para-xylene and later desorbing the para-xylene using a desorbent, as the process stream. The SMB process may use a single adsorbent that has the best characteristics for preferentially adsorbing para-xylene, or multiple adsorbents.

It is preferred to operate the adsorption zone at conditions which include a temperature between about 120° C. and 200° C. (249° F. to 392° F.) as this provides better selectivity and capacity. Another important operational variable is the water content of the molecular sieve. This variable is necessary for mass transfer considerations, but there is a tradeoff in that water enhances mass transfer of the para-xylene, but reduces capacity of both the para-xylene and total $C_8$ aromatic capacity. Therefore, a balance must be achieved to optimize the process. As a commercial process operates continuously with the adsorbent confined within the chambers the acknowledged method of operation includes adding water, as required, to the feed stream. The level of hydration of the adsorbent is reported on a volatile free basis or by a measurement referred to as Loss on Ignition (LOI) as described in U.S. Pat. No. 5,900,523. In the LOI test the volatile matter content of the zeolitic adsorbent is determined by the weight difference obtained before and after drying a sample of the adsorbent at 900° C. under an inert gas purge such as nitrogen for a period of time sufficient to achieve a constant weight. Other operating variables include the L3/A ratio and the A/F ratio. The L3/A ratio is the ratio of liquid flow through zone 3 of the SMB system to the rate of simulated circulation of selective pore volume through the process. The A/F is the ratio the rate of simulated circulation of selective pore volume through the process to the volumetric feed rate of the feed mixture. The A/F ratio sets an operating curve, specific to a particular L3 rate. Operating with an A/F ratio of about 0.3 to about 0.7 is preferred. A process unit designed for normally producing a high purity product (e.g., 99%) will operate at the higher end of this general range.

Absorbents known in the art include an X zeolite, and preferably the adsorbent is barium substituted X zeolite, or BaX. They also include a Y zeolite, and preferably the adsorbent is potassium substituted Y zeolite, or KY. X zeolites are known in the art for use in the separation of para-xylene as described in U.S. Pat. No. 6,706,938 and is incorporated by reference in its entirety. Y-zeolites are known in the art and are described in U.S. Pat. Nos. 4,842,836, 4,965,233, 6,616,899, and 6,869,521 and which are incorporated by reference in their entirety.

The separated para-xylene product from the para-xylene separation zone 39 may be removed as stream 40. Some of the remaining xylenes and ethylbenzene may be returned to the aromatics recovery unit 27 via stream 41. Additionally, some of the remaining xylenes and ethylbenzene may be passed to an isomerization zone 43 via stream 42. Stream 42 may include non-equilibrium xylene and ethylbenzene. These aromatic compounds are in a non-equilibrium mixture, i.e., at least one $C_8$ aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be the para-isomers, due to the previous separation thereof. Generally the mixture will have an ethylbenzene content of about 14 mass-% of $C_8$ compounds, an ortho-xylene content of 0 to about 35 mass-%, a meta-xylene content of about 20 to about 95 mass-%, and a para-xylene content of 0 to about 30 mass-%.

Especially advantageous as the xylene/ethylbenzene isomerization catalyst is a catalyst containing 12-membered rings and 10-membered rings in the same 3-dimensional structure. Commercial utility is typically seen in aluminosilicate structures which are synthesized in hydroxide media with readily available structure directing agents. Zeolites which contain both 12-membered and 10-membered rings in 3-dimensional structures belong to the CON, DFO, IWR, IWW and MSE structure types. The synthesis of CIT-1, a zeolite of the CON structure type, is described in U.S. Pat. No. 5,512,267 and in J. Am. Chem. Soc. 1995, 117, 3766-79 as a borosilicate form. After synthesis, a subsequent step can be undertaken to allow substitution of Al for B. The zeolites SSZ-26 and SSZ-33, also of the CON structure type are described in U.S. Pat. No. 4,910,006 and U.S. Pat. No. 4,963,337 respectively. SSZ-33 is also described as a borosilicate.

One particular zeolite of the MSE structure type, designated MCM-68, was disclosed by Calabro et al. in 1999 (U.S. Pat. No. 6,049,018). This patent describes the synthesis of MCM-68 from dication directing agents, N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5R,6S-dipyrrolidinium dication. MCM-68 was found to have at least one channel system in which each channel is defined by a 12-membered ring of tetrahedrally coordinated atoms and at least two further independent channel systems in which each channel is defined by a 10-membered ring of tetrahedrally coordinated atoms wherein the number of unique 10-membered ring channels is twice the number of 12-membered ring channels, see Patent Application Publication no. US 2009/318696 A1.

The non-equilibrium mixture, in the presence of hydrogen supplied via line 44, is contacted with an isomerization catalyst as described above. Contacting may be effected using the catalyst system in a fixed-bed system, a moving-bed system, a fluidized-bed system, and an ebullated-bed system or in a batch-type operation. In view of the danger of attrition loss of valuable catalysts and of the simpler operation, it is preferred to use a fixed-bed system. In this system, the feed mixture is preheated by suitable heating means to the desired reaction temperature, such as by heat exchange with another stream if necessary, and then passed into an isomerization zone containing catalyst. The isomerization zone may be one or more separate reactors with suitable means therebetween to ensure that the desired isomerization temperature is maintained at the entrance to each zone. The reactants may be contacted with the catalyst bed in upward-, downward-, or radial-flow fashion.

The isomerization is conducted under isomerization conditions including isomerization temperatures generally within the range of about 100° to about 550° C. or more, and preferably in the range from about 150° to 500° C. The pressure generally is from about 10 kPa to about 5 MPa absolute, preferably from about 100 kPa to about 3 MPa absolute. The isomerization conditions comprise the presence of hydrogen in a hydrogen to hydrocarbon mole ratio of between about 0.5:1 to 6:1, preferably about 1:1 or 2:1 to 5:1. A sufficient mass of catalyst comprising the catalyst (calculated based upon the content of molecular sieve in the catalyst composite) is contained in the isomerization zone to provide a weight hourly space velocity with respect to the liquid feed stream (those components that are normally liquid at STP) of from about 0.1 to 50 hr$^{-1}$, and preferably 0.5 to 25 hr$^{-1}$.

The isomerization zone product stream 45 may thereafter be passed to one or more fractionation columns, which may include a deheptanizer column producing $C_7$ overhead products (stream 47) and recycling the $C_8$ products back to the xylene fractionator 36 (stream 46A), and a stripper column 49 (fed by a side cut 48 of the depheptanizer column 46) that recycles its product back to the aromatics recovery unit 27. As such, the isomerization zone isomerized the non-equilibrium xylenes and ethylbenzene to produce additional para-xylene, which is then recycled back to the fractionator 36 and then the para-xylene separation zone 39 for additional separation and recovery of para-xylene, thereby increasing process yields.

Reference is now made to FIG. 1B, which illustrates the transalkylation portion 10B of system 10. As noted above, stream 34, which is the extracted toluene produced by the toluene fractionation column 33, is used as a feed for the transalkylation portion 10B. Additionally, the bottoms stream 38 from the xylene fractionation column 36 is used in this portion 10B. Stream 34 is passed to a transalkylation/disproportionation zone 51. The feed to the transalkylation/disproportionation zone includes the toluene from stream 34, as well as $C_9$ aromatics that are obtained from the stream 38 after processing through a heavy aromatics column 67 (resulting in an enriched $C_9$ stream 69), as will be described in greater detail below. $C_{10+}$ hydrocarbons may also be present.

The stream of toluene 34 and the stream enriched in $C_9$ aromatics 69, together with or separate from each other, are fed to the transalkylation/disproportionation reaction zone 51. For example, the feed material of the reaction zone 51 includes by weight 10-90% of toluene, 10-90% of $C_9$ aromatics, and 0-5% of $C_{10+}$.

The streams 34 and 69 of toluene and enriched in $C_9$ aromatics are subjected to the disproportionation and transalkylation reactions in the presence of hydrogen (provided via stream 52) in the reaction zone 51. The reactions produce a product mixture including benzene, $C_8$ aromatics, and $C_{10+}$ hydrocarbons. The reactions in the reaction zone 51 proceed in the presence of catalysts. The catalysts employed in the reaction zone 51 can be one or more catalysts known in the art for these purposes, for example, a metal-containing zeolite. Of the catalyst, the metal can be one or more selected from the group consisting of Bi, Mo, Fe, Co, Ni, Pt, Ag, Pd, Re and Au, and the zeolite can be one or more selected from the group consisting of Y-type zeolite, mordenite, β-zeolite and ZSM-type zeolite. During reactions, the pressure is 1.0-5.0 MPa, the temperature is 300-480° C., and hydrogen/hydrocarbon molar ratio is 1-10. The space velocity by weight is maintained at 0.5-10 h$^{-1}$. The products of the disproportionation and transalkylation reactions are removed from the reaction zone 51 via the stream 53.

A stripper column 54 is provided to further process product stream 53. Stripper column 53 removes light ends as an overhead fraction, a side-cut stream 57 is transferred to a further stripper column associated with a dealkylation zone (as will be discussed in greater detail below), and a bottoms product stream 56 is transferred to a benzene fractionation column 58 followed by a toluene fractionation column 61, similar to columns 30 and 33, described above (benzene is removed via overhead stream 59, bottoms stream 60 feeds column 61, a toluene overhead product from column 61 is recycled back to the reaction zone 51 via stream 62, and a bottoms product stream 63 from the toluene column 61 is processed in a xylene fractionation column 64. Xylene fractionation column produces an overhead stream 65 including mixed xylenes and ethylbenzene, and a bottoms product stream 66 including heavier aromatic hydrocarbons.

Returning to the discussion of stream 38, which derives from the bottoms product of xylene fractionation column 36, stream 38 joins like stream 66 (both being bottoms of a xylene fractionation column) and proceeds to the aforementioned heavy aromatics column 67. Heavy aromatics column 67, as mentioned above, produces as an overhead stream 69 the enriched $C_9$ aromatics product (the portion of stream 69 not need for use in the reaction zone 51 may be removed from the system as a product stream 69A, and may be suitable for use in various gasoline grades, for example) and as a bottoms stream 68 a heavy aromatics product, which may be removed from the system for uses in other products and/or processes.

The overhead stream 65 of the xylene fractionation column 64 proceeds to a para-xylene separation zone 70. As with para-xylene separation zone 39, discussed above, para-xylene separation zone may operate according to known SMB technology, using like catalysts and like processing conditions. The para-xylene product is removed from zone 70 via stream 71, some of the mixed xylenes and ethylbenzene not separated proceed via stream 72 to the aromatics recovery unit 27, and the rest of the mixed xylenes and ethylbenzene proceed via stream 73 to a dealkylation zone 74.

As initially noted above, the ethylbenzene present as a fraction of $C_8$ compounds may be about 1% in this transalkylation portion 10B of system 10. These aromatic compounds are in a non-equilibrium mixture, i.e., at least one $C_8$ aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be the para-isomers, due to the previous separation thereof. Generally the mixture will have an ethylbenzene content of about 1 mass-% of $C_8$ compounds, an ortho-xylene content of 0 to about 35 mass-%, a meta-xylene content of about 20 to about 95 mass-%, and a para-xylene content of 0 to about 30 mass-%.

The catalysts used in the EB dealkylation zone 74 include a molecular sieve having a pore diameter of from about 4 to 8 angstroms, and a platinum hydrogenation component in an amorphous aluminum phosphate binder. Examples of molecular sieves include those having $Si:Al_2$ ratios greater than about 10, and often greater than about 20, such as the MFI, MEL, EUO, FER, MFS, MTT, MTW, TON, MOR, UZM-8 and FAU types of zeolites. Pentasil zeolites such as MFI, MEL, MTW and TON are preferred, and MFI-type zeolites, such as ZSM-5, silicalite, Borolite C, TS-1, TSZ, ZSM-12, SSZ-25, PSH-3, and ITQ-1 are especially preferred. The zeolite is combined with binder for convenient formation of catalyst particles. The relative proportion of zeolite in the catalyst may range from about 1 to about 99 mass-%, with about 2 to about 90 mass-% being preferred.

The binder should be uniform in composition and relatively refractory to the conditions used in the process. Suitable binders include inorganic oxides such as one or more of alumina, aluminum phosphate, magnesia, zirconia, chromia, titania, boria and silica. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; which components can be added to the composite at any suitable point.

A preferred binder or matrix component comprises an amorphous phosphorous-containing alumina (hereinafter referred to as aluminum phosphate) component. The atomic ratios of aluminum to phosphorus in the aluminum phosphate binder/matrix generally range from about 1:10 to 100:1, and more typically from about 1:5 to 20:1. Preferably the aluminum phosphate has a surface area of up to about 450 $m^2$/g, and preferably the surface area is up to about 250 $m^2$/g. See, for instance, U.S. Pat. No. 6,143,941.

The non-equilibrium mixture, in the presence of hydrogen supplied via line 75, is contacted with an EB dealkylation type catalyst as described above. Contacting may be effected using the catalyst system in a fixed-bed system, a moving-bed system, a fluidized-bed system, and an ebullated-bed system or in a batch-type operation. The dealkylation zone 74 may be one or more separate reactors with suitable means therebetween to ensure that the desired isomerization temperature is maintained at the entrance to each zone. The reactants may be contacted with the catalyst bed in upward-, downward-, or radial-flow fashion.

The dealkylation zone product stream 76 may thereafter be passed to one or more fractionation columns, which may include a deheptanizer column producing $C_7$ overhead products and recycling the $C_8$ products back to the xylene fractionator 64 (stream 79), and a stripper column 80 (fed by a side cut 78 of the dephepanizer column 77 and stream 57 from the stripper 54, as discussed above) that recycles its product back to the aromatics recovery unit 27 via stream 82. Additionally, light ends leave the system portion 10B via overhead stream 81 from the stripper column 80. As such, the dealkylation zone isomerizes the non-equilibrium xylenes and dealkylates the ethylbenzene to produce additional para-xylene, which is then recycled back to the fractionator 64 and then the para-xylene separation zone 70 for additional separation and recovery of para-xylene, thereby increasing process yields.

Accordingly, in the present disclosure, after separation of para-xylene, the non-equilibrium mixture of xylenes and ethylbenzene are processed in two separate zones (43 and 74) that are optimized based on the amount of ethylbenzene to be expected in the respective stream. For the reforming portion 10A, the zone 43 is an isomerization zone that isomerizes the xylenes and ethylbenzene. For the transalkylation portion 10B, the zone 74 is a dealkylation zone that isomerizes the xylenes and dealkylates the ethylbenzene. Accordingly, the mixed xylenes and EB produced in the reforming portion are preferentially processed using an EB isomerization based process; at about 14% of $C_8$ aromatic compounds, the $C_8$ aromatics in reformate have the highest EB concentration, and processing this stream with an EB isomerization catalyst improves the overall yield to para-xylene. In contrast, the mixed xylenes produced in transalkylation portion, at about 1% of the $C_8$ aromatics compounds, are preferentially processed using an EB dealkylation based catalyst. Because this mixed xylene stream has very low concentration of EB, processing this stream with a high efficiency EB dealkylation lowers utilities and capital costs. Thus, as opposed to combining the mixed xylene stream, which as noted above is sometimes done in the prior art, the utilities and investment cost of this "hybrid" complex are significantly reduced, with improved product yield.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:
1. A method for processing a naphtha-containing hydrocarbon stream comprising the steps of:
hydrotreating a naphtha-containing hydrocarbon stream in the presence of a catalyst active for removal of heteroatoms;
reforming the naphtha-containing hydrocarbon stream in the presence of a catalyst containing a porous support, a binder, one or more group VIII noble metal selected from platinum, iridium, rhodium, and palladium, and a promoter element selected from gallium, germanium, indium, tin, thallium, and lead to produce a first mixed-xylene and ethylbenzene-containing stream and a toluene stream, and wherein the toluene stream is produced using aromatics recovery processes;
separating para-xylene from the first mixed-xylene and ethylbenzene-containing stream to produce a first non- equilibrium xylene and ethylbenzene stream, wherein separating para-xylene is performed using simulated moving bed processes;

isomerizing the first non-equilibrium xylene and ethylbenzene stream in the presence of an isomerization catalyst containing a first concentration of precious metal to produce additional para-xylene;

transalkylating the toluene stream with a C9+ aromatic hydrocarbons stream in the presence of catalyst containing a zeolite selected from Y zeolite, Beta zeolite, mordenite, and ZSM-type zeolite and a metal selected from Bi, Mo, Fe, Co, Ni, Pt, Ag, Pd, Re, and Au to produce a second mixed-xylene and ethylbenzene-containing stream, wherein the first mixed-xylene and ethylbenzene-containing stream comprises a greater proportion of ethylbenzene than does the second mixed-xylene and ethylbenzene-containing stream;

separating para-xylene from the second mixed-xylene and ethylbenzene-containing stream to produce a second non-equilibrium xylene and ethylbenzene stream, wherein separating para-xylene is performed using simulated moving bed processes; and isomerizing the second non-equilibrium xylene and ethylbenzene stream using an ethylbenzene dealkylation and xylene isomerization catalyst having a second concentration of precious metal to dealkylate ethylbenzene and isomerize xylenes to produce additional para-xylene; wherein the first concentration of precious metal is higher than the second concentration of precious metal.

2. The method of claim 1, wherein hydrotreating comprises removing sulfur species.

3. The method of claim 2, wherein hydrotreating further comprises removing nitrogen species.

4. The method of claim 1, wherein the toluene stream is further produced using a first distillation column that removes benzene as an overhead product.

5. The method of claim 1, wherein the toluene stream is further produced using a second distillation column that removes toluene as an overhead product.

6. The method of claim 1, wherein the naphtha-containing hydrocarbon stream is derived from a plurality of naphtha sources.

7. The method of claim 1, wherein the simulated moving bed processes are performed in the presence of a para-xylene adsorbent material.

* * * * *